(12) United States Patent
Cawthorne

(10) Patent No.: US 9,358,196 B2
(45) Date of Patent: Jun. 7, 2016

(54) SPRAYABLE DEPILATORY COMPOSITION AND A METHOD OF USE

(75) Inventor: Lee Cawthorne, Hull (GB)

(73) Assignee: RECKITT BENCKISER (UK) LIMITED, Slough, Berkshire (GB)

( * ) Notice: Subject to any disclaimer, the term of this patent is extended or adjusted under 35 U.S.C. 154(b) by 1039 days.

(21) Appl. No.: 12/083,329

(22) PCT Filed: Oct. 16, 2006

(86) PCT No.: PCT/GB2006/003821
§ 371 (c)(1),
(2), (4) Date: Apr. 7, 2008

(87) PCT Pub. No.: WO2007/042829
PCT Pub. Date: Apr. 19, 2007

(65) Prior Publication Data
US 2009/0068119 A1    Mar. 12, 2009

(30) Foreign Application Priority Data
Oct. 14, 2005   (GB) .................................. 0520930.9

(51) Int. Cl.
*A61K 8/04*   (2006.01)
*A61Q 9/04*   (2006.01)
*A61K 8/46*   (2006.01)
*A61K 8/34*   (2006.01)
*A61K 8/39*   (2006.01)

(52) U.S. Cl.
CPC . *A61K 8/46* (2013.01); *A61K 8/046* (2013.01); *A61K 8/342* (2013.01); *A61K 8/39* (2013.01); *A61Q 9/04* (2013.01); *A61K 2800/87* (2013.01)

(58) Field of Classification Search
CPC ......... A61K 8/46; A61K 8/046; A61K 8/342; A61K 8/39; A61K 2800/87; A61Q 9/04
See application file for complete search history.

(56) References Cited

U.S. PATENT DOCUMENTS

| 3,248,235 | A  | * | 4/1966  | Pryor et al. ....................... 106/3 |
| 3,527,559 | A  |   | 9/1970  | Sliwinski |
| 6,098,846 | A  | * | 8/2000  | Yazawa et al. .................. 222/95 |
| 6,146,620 | A  |   | 11/2000 | Janowski |
| 6,150,318 | A  | * | 11/2000 | Silvester et al. ............. 510/284 |
| 6,479,043 | B1 | * | 11/2002 | Tietjen et al. .................... 424/73 |
| 2003/0118535 | A1 |   | 6/2003 | Lustbader et al. |
| 2004/0219118 | A1 |   | 11/2004 | Slavtcheff et al. |
| 2006/0034874 | A1 | * | 2/2006 | Winston et al. ............... 424/401 |

FOREIGN PATENT DOCUMENTS

GB    1381669    *    1/1975

OTHER PUBLICATIONS

"Dynamic, Absolute, Kinematic Viscosity" accessed online at www.engineeringtoolbox.com/dynamic-absolute-kinematic-viscosity-d_412.html on Apr. 11, 2011.*
McGraw-Hill Encyclopedia of Science & Technology, 9th edition, McGraw-Hill: New York, 2002, pp. 303.*
MacMillan Encyclopedia of Physics, vol. 4, Simon & Schuster: London, 1996, pp. 1677.*
PCT International Search Report and the Written Opinion of the International Searching Authority, PCT/GB2006/003821, dated Feb. 12, 2007.
Combined Search and Examination Report under Sections 17 and 18(3) dated Mar. 1, 2006.

* cited by examiner

*Primary Examiner* — Mina Haghighatian
(74) *Attorney, Agent, or Firm* — Troutman Sanders LLP; Ryan A. Schneider; Troy S. Kleckley

(57) ABSTRACT

A sprayable depilatory composition including a depilatory agent; a surfactant present in the range 0.1% to 5.0% by weight of the composition, wherein the composition has an initial viscosity substantially less than about 7.00 Pas.

11 Claims, 1 Drawing Sheet

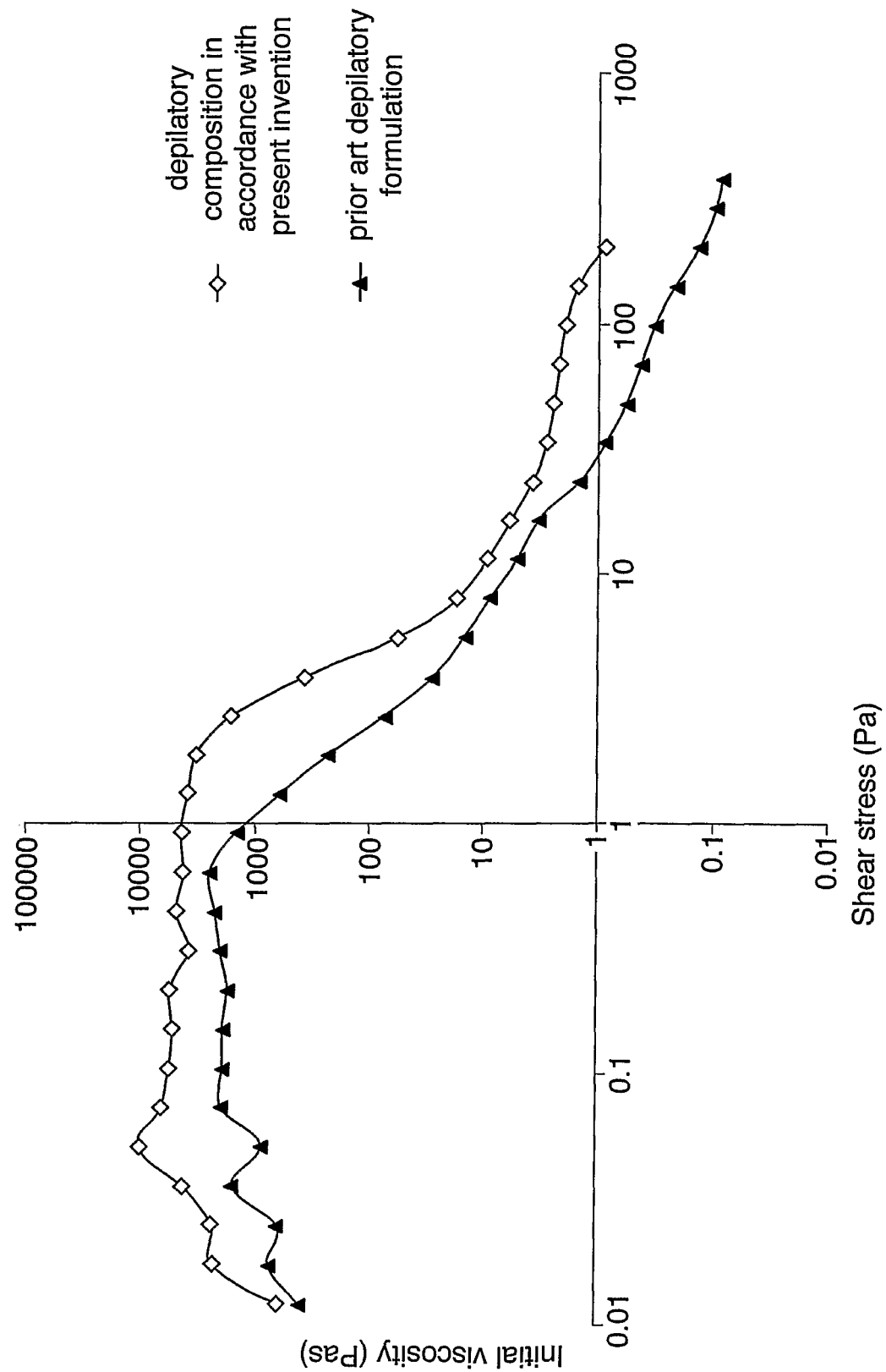

SPRAYABLE DEPILATORY COMPOSITION AND A METHOD OF USE

The present invention relates to compositions, their preparation, and methods for their use in removing hair from the skin of humans. In particular, the present invention is concerned with a depilatory composition.

Compositions for removing superfluous body hair are known and are of various types. One type of composition requires initial heating before being applied to the skin in a generally molten state. It is then allowed to solidify before being removed from the skin together with unwanted hair. This is known in the art as epilation, as the hairs are uprooted from the skin.

Another type of composition is in the form of a cream, which can be applied to the skin at room temperature. The cream includes a substance that degrades hair keratin. Conventionally, the compositions are applied to the skin where unwanted hair is present, then left in place for a predetermined time to allow the keratin in the hair to become degraded. The composition along with degraded hair is then removed from the skin, usually with a tool such as a sponge or wipe or spatula. Such compositions are known in the art as depilatory compositions.

If the depilatory composition is left in contact with the skin for excessive lengths of time, there is a risk that the composition may cause irritation of the skin in some users. If it is present for too short a time, degradation of keratin may be inadequate, leading to only partial removal of the unwanted hair. In this specification, the period the composition must be left in contact with the hairy skin to achieve adequate hair degradation is referred to as the degradation period. Typical degradation periods are in the range 2 to 15 minutes.

In the art, the trend has been to make depilatory compositions sufficiently viscous so that they will stay in place on desired region of skin where superfluous hair removal is desired, without slipping to other regions of skin or falling off during the degradation period. In parallel, there has also been a trend to make the compositions easier to rinse from the skin, so that once the degradation period is over, the composition and degraded hairs can be rinsed easily from the skin. See for example EP0855900.

WO 99/02125 discloses depilatory compositions in the form of oil-in-water emulsions. The preferred depilatory compound is cited as potassium thioglycolate. A pH regulator is present, the preferred pH regulator being lime (calcium hydroxide).

However, a problem with prior art depilatory compositions is that they often require application by hand or by using an applicator. Both use of an applicator and a hand is often considered undesirable and/or messy by users of depilatory compositions.

It has been known to apply depilatory compositions to the area to be treated by pump dispenser. However, a problem associated with such delivery systems is that the depilatory composition is not evenly applied to the desired area and an applicator is still required to spread the composition over the desired area.

It is therefore an aim of the present invention to alleviate at least some of the disadvantages identified above.

It is a further aim of the present invention to provide a depilatory composition which reduces the requirement for application by hand and/or a depilatory tool.

It is yet a further aim of the present invention to provide a depilatory composition which is capable of being dispenses by a pump-type mechanism.

Therefore, according to a first aspect of the present invention, there is provided a sprayable depilatory composition including a depilatory agent; a surfactant present in the range 0.1% to 5.0% by weight of the composition, wherein the composition has an initial viscosity substantially less than about 7.00 Pas.

Preferably, the composition has a viscosity less than about 6.5 Pas, further preferably less than about 5.00 Pas. The composition typically has a viscosity of more than about 1.0 Pas, such as more than about 1.5 Pas. It is particularly preferred that the composition has a viscosity substantially in the range of from about 1.5 Pas to about 4.5 Pas.

Typically, prior art depilatory compositions have a viscosity of about 65 Pas to about 160 Pas. Such high viscosities have previously been thought to be advantageous as it has been desirable to ensure the depilatory composition is sufficiently viscous to prevent it from slipping off the skin during use.

The reduced amount of surfactant present in the composition results in a reduced viscosity when compared to standard depilatory compositions. Advantageously, the reduced viscosity permits the composition to be pumped or forced under pressure through a spray nozzle without losing any efficacy. Additionally, the composition is capable of substantially covering the desired area without the requirement of the user to spread with a hand or tool.

Advantageously, the composition has a structure which is capable of being broken down whilst under stress (which is typically due to the composition being forced through a nozzle of a dispenser) but substantially regaining its original structure once it has passed through a nozzle.

Advantageously, the composition according to the present invention is capable of being sprayed through a pump-type spray which are commonly known in the field. As a result of the viscosity characteristics of the composition it does not lose efficacy as it is pumped through a nozzle.

The surfactant may be anionic, cationic or non-ionic, however it is preferred that the surfactant is non-ionic. Examples of suitable surfactants include cetearyl phosphate, cetearyl alcohol, stearyl ether, cetearyl alcohol, cetearyl glycoside, cetostearyl alcohol and/or ceteareth 20. It is envisaged that the surfactant may include one or more of compound.

The one or more surfactant is preferably present in an amount less than 4% by weight of the composition, further preferably less than about 3.8% by weight, such as around 3.5% by weight of the composition.

Preferably, when the composition includes ceteareth 20 it is present in an amount of not more than about 1.0% by weight of the composition, such as less than about 0.9% by weight of the composition.

Preferably, when composition includes stearyl ether it is present in an amount of less than 0.8% by weight of the composition, further preferably less than about 0.6% by weight of the composition.

Preferably, when the composition includes cetearyl alcohol it is present in an amount of less than 2.5% by weight of the composition, further preferably less than about 2.3% by weight of the composition. It is particularly preferred that the cetearyl alcohol is present in an amount less than about 2.2% by weight of the composition. It is further particularly preferred that the cetearyl alcohol is present in an amount of less than about 0.6% by weight of the composition.

Preferably, the depilatory agent is a compound capable of degrading keratin. The depilatory agent may include one or more depilatory actives. Suitable depilatory actives are sulfhydryl compounds, meaning a compound having an —S—H group. Preferred sulfhydryl compounds include thioglycolic acid, cysteine, glutathione, N-acetyl-L-cysteine, lipoic acid, thiosalicylic acid, and thiolactic acid and cosmetically- and/or pharmaceutically-acceptable salts thereof More preferred sulfhydryl compounds include thioglycolic acid, cysteine, glutathione and N-acetyl-L-cysteine and cosmetically- and/or pharmaceutically acceptable salts thereof. The most preferred sulfhydryl compound is thioglycolic acid and cosmetically- and/or pharmaceutically-acceptable salts thereof. As used herein, "cosmetically- and/or pharmaceutically-acceptable salts" of the sulfhydryl compounds include, but are not limited to alkali metal salts, e.g., sodium, lithium, rubidium and potassium salts; alkaline earth metal salts, e.g., magnesium, calcium and strontium salts; non-toxic heavy metal salts, e.g., aluminum salts and zinc salts; boron salts; silicon salts; ammonium salts; trialkylammonium salts, e.g., trimethylammonium and triethylammonium; and tetralkylonium salts.

The depilatory composition may include 0.01 to 30% by weight of the depilatory active, preferably 0.05% to 20% by weight, more preferably 0.01% to 15% by weight of the depilatory active. It is particularly preferred that the depilatory active is present in the composition in the range 8.0% to 14% by weight.

Preferred cosmetically- and/or pharmaceutically-acceptable salts of the sulfhydryl compound include sodium, potassium and calcium salts. Most preferred salts of the sulfhydryl compound are potassium and calcium salts.

Preferred depilatory actives are thioglycolates, or their precursor thioglycolic acid. Most preferred is potassium thioglycolate, which may be produced by mixing thioglycolic acid with potassium hydroxide.

Optionally, the composition includes an accelerator that will accelerate the keratin degradation reaction. Suitable accelerators include urea, thiourea, dimethyl isosorbide, ethoxydiglycol and methyl propyl diol. Preferably the accelerator is urea or methyl propyl diol. The composition according to the invention preferably comprises from 5% to 15% by weight, more preferably 7% to 10% by weight of an accelerator.

It is particularly preferred for the composition to comprise a pH regulator to assist in activating the depilatory agent, particularly when the depilatory agent is a sulfhydryl compound. Preferably the quantity and type of pH regulator is chosen to maintain the pH of the composition at a value greater than 5, preferably greater than 7, more preferably from 8 to 13, most preferably from 10 to 12.9, especially from 12 to 12.7. For example, by ensuring that the pH is about 12.1 to 12.7, depilation can occur within about 5 minutes, as desired by the user, without causing undue irritation. Higher pH levels can lead to irritation problems with some users.

The pH regulator preferably is in the continuous aqueous phase (between the hydrophobic particles) when present. Examples of the pH regulator include arginine (especially L-arginine), silicates (e.g. sodium or potassium silicate), calcium hydroxide and polyethyleneimine. Mixtures of pH regulators may be used. It is particularly preferred for the pH regulator also to include calcium hydroxide in an amount from 2 to 4% by weight of the composition. The pH regulator may be dissolved in the aqueous phase of the composition or may be present as solid particles dispersed throughout the composition.

Compositions according to the invention comprise hydrophobic particles distributed as an emulsion (an oil-in-water emulsion) in an aqueous continuous phase which is a liquid at 25° C. By aqueous it is meant that the continuous phase comprises at least 50% by weight of water, preferably 70% by weight or more based on the total weight of the continuous phase. The amount of water in the composition as a whole will typically be from 40% to 80% by weight of the composition.

The depilatory composition of the present invention may additionally include one or more oils. The oil may act as a moisturizer and/or humectant. Suitable oils include allantoin, shea butter, cocoa butter, goa butter, kukui nut oil, coconut oil, castor oil, palm oil, olive oil, avocado oil, apricot kernel oil, sweet almond oil and hemp oil. Other oils include thick mineral oils (eg. paraffin oil), isohexane and sunflower seed oil. Preferably, the composition includes shea butter, thick mineral oil and/or sweet almond oil.

The oil may be present in the composition in an amount 0.01% to about 1.5% by weight of the composition, preferably in an amount less than about 1.0% by weight, further preferably less than about 0.1% by weight of the composition.

The depilatory composition may optionally include a skin conditioning active. Such actives may be present in an amount of from 0.01 to 10 weight % of the solid depilatory composition. Preferably, the skin conditioning active is present in an amount of 0.1 to 5 weight %, for example, 0.1 to 1 weight %. Suitable skin conditioning actives include aloe vera, shea butter, lotus flower milk, glycerine, petrolatum, coconut oil and silk extracts.

The depilatory composition may optionally include one or more vitamins, such as Vitamin E. Vitamins may be present in an amount of from 0.01 to 10% by weight of the depilatory composition. Preferably, the one or more vitamins are present in an amount of 0.01 to 5%, for example 0.1 to 0.3% weight %.

The composition may further include other ingredients that are conventionally present in depilatory compositions, such as perfumes, oils, pigments (such as titanium dioxide) and thickeners (such as clay).

Suitable clays for thickening may include organophilic and layered clay minerals belonging to the geological classes of the smectites, the kaolins, the illites, the chlorites, the attapulgites and the mixed layer clays. Typical examples of specific clays belonging to these classes are: 1) smectites, e.g. montmorillonite, bentonite, pyrophyllite, hectorite, saponite, sauconite, nontronite, talc, beidellite; 2) illites, e.g., bravaisite, muscovite, paragonite, phlogopite; 3) chlorites, e.g., corrensite, penninite, donbassite, sudoite; 4) attapulgites, e.g., sepiolite, and polygorskyte.

The layered clay minerals may be either naturally occurring or synthetic. Preferred clay minerals for use in the present invention are natural or synthetic smectites and attapulgites, (particularly the hectorites, montmorillonites and bentonites,) and of these the hectorites are especially preferred. Many of the above clays are available commercially, and typical examples of commercial hectorites are the Laponites ex Laporte Industries Ltd., England; Veegum Pro and Veegum F ex R. T. Vanderbilt, USA; and the Barasyms, Macaloids and Propaloids ex Baroid Division, National Lead Company, USA. If a clay is used for thickening, it is preferably in an amount of from 0.1 to 10% by weight, more preferably from 0.1 to 1% by weight of the composition.

The inclusion of a clay, preferably sodium lithium magnesium silicate, is particularly advantageous, since this provides lithium, sodium and magnesium ions for the buffer system and improves the efficiency of depilation. It is particularly preferred if the clay is a synthetic hectorite clay such as Laponite™.

Other optional water-soluble thickening agents which may be used include Carbomer™ (Acrylic acid polymer, preferably cross-linked), acrylic polymer emulsions (e.g. acrylate/steareth-20 methracylate copolymer), polysaccharides, cellulose based thickeners or natural thickeners such as gum arabic, alginates, carrageenan, locust bean gum, xanthan gum and polyvinyl alcohol. Mixtures of thickeners may be used.

The composition may further comprise a source of alkalinity, for example an alkali metal hydroxide or potassium hydroxide. Desirably the PH of the composition of the present invention is at least 12, more preferably at least 12.4.

Preferably the alkali metal hydroxide is present in an amount 1.0% by weight to about 7.0% by weight of the composition. Further preferably in the range from about 2.0% to about 6% by weight. A particularly preferred range is 3.0% to 4.5% by weight of the composition.

The depilatory composition may, for example, be in the form of an oil-in-water emulsion, a water-in-oil emulsion, a micro-emulsion, a multiple emulsion, a lotion, a cream, a gel or a foam.

Accordingly, the present invention extends to a method of depilation which includes the steps of:
 a. providing a dispenser having a spray nozzle, the dispenser containing the depilatory composition according to the first aspect of the present invention;
 b. dispensing the depilatory composition from the dispenser through the nozzle so as to form a substantially uniform layer of composition over an area of hairy skin;
 c. permitting the composition to remain on the skin for a residence time so as to degrade the hairs;
 d. removing the composition together with the depilated hairs at the end of the residence time;
 e. rinsing the skin.

Preferably, the residence time is less than 5 minutes, more preferably not more than 4 minutes. Preferably, the residence time is at least 1 minute.

According to a third aspect of the present invention, there is provided a use of a composition according to the first aspect of the invention to degrade hair.

The composition according to the present invention may be prepared, for example, by mixing the various components together, preferably at a temperature not exceeding 85° C. More preferably all of the compounds, excluding the depilatory active are first mixed together at this elevated temperature, the resultant composition is actively or passively cooled and the depilatory compound added to the cooled composition at a temperature of from 15° C. to 40° C., preferably at ambient temperature (eg. about 20° C.). The source of alkalinity, such as the alkali metal hydroxide may be added at any stage of the process, but preferably after the depilatory compound is added.

Depilatory formulations known in the prior art are typically applied by foam dispensing or as a cream, they are not suitable for being sprayed as they are incapable of being sprayed in a sufficiently thin and uniform manner on the skin.

Advantageously, the compositions of the present invention are thin enough to be sprayed onto the surface of a users skin but when it is on the skin it becomes viscous enough to stay on the skin during use.

It is particularly preferred that is capable of being dispensed through any spray dispensing apparatus known in the art, suitable systems include but are not limited to bag-on-valve technology or mechanically pumped spraying.

The dispensing apparatus used for distributing the composition of the present invention may be a pressurised apparatus typically having an internal pressure in the range 4 to 9 bar at first use or prior to first use. Preferably less than 8.5, more preferably less than 8, such as less than 7.5 or less than 6.5. It is particularly preferred that the pressure is less than 6 bar. Preferably the pressure at first use is greater than 4.2 bar, further preferably greater than 4.5 bar. It is particularly preferred that the internal pressure at first use is in the range 4.8 to 5.8 bar.

Preferably the dispensing apparatus has an actuator having a diameter in the range 0.010" to 0.017", preferably 0.011" to 0.016", further preferably 0.012 to 0.015".

The dispensing apparatus typically as an internal pressure, during use, in the range 3 to 9 bar.

According to a particularly preferred embodiment the dispensing apparatus has an actuator having a spray diameter in the range 5 to 14 cm at a distance of approx 10 cm.

Therefore, the present invention extends to a hair removal system which includes:
 a dispensing apparatus having an internal reservoir and an actuator having a diameter in the range 0.010" to 0.017", the dispensing apparatus having an internal pressure in the range 4 to 9 in first use or prior to first use; and a depilatory composition.

The dispensing system is substantially as described hereinbefore.

The depilatory composition is substantially as described hereinbefore.

The present invention will now be described by way of example only, with reference to the accompanying example.

EXAMPLE 1

A depilatory composition was prepared from the following ingredients:

| Ingredients | % Weight |
|---|---|
| Aqueous Phase | |
| Deionised Water | 45.67 |
| Titanium Dioxide Paste | 0.8 |
| Calcium Hydroxide | 3.3 |
| Magnesium Trisilicate | 0.4 |
| Fragrance Pack | 0.85 |
| Sodium Gluconate | 0.15 |
| Spray Dried Silica | 0.03 |
| Oily Phase | |
| Cetearyl Alcohol | 2.1 |
| Ceteareth-20 | 0.5 |
| Thick Mineral Oil | 0.075 |
| Sweet Almond Oil | 0.075 |
| PPG-15 Stearyl Ether | 0.45 |
| Urea Pre-Mix | |
| Deionised Water | 26.3 |
| Urea | 5.5 |
| Acrylates Copolymer | 0.1 |
| Potassium Thioglycolate | 12.7 |
| Potassium Hydroxide | 1.0 |
| TOTAL | 100 |

The method of preparation of the composition was to form a mixture of the aqueous phase, the oily phase and the urea premix by blending and stirring for 40 minutes at a temperature maintained between 65° C. and 85° C.; passively cooling the composition to ambient temperature; mixing in the potassium thioglycolate and potassium hydroxide at ambient temperature, and stirring under conditions which do not include a temperature increase.

As a result of the reduced viscosity the composition according to the present invention can be pumped through a spray nozzle at a rate of about 0.25 ml per stroke.

The formulation of Example 1 was arranged in a bag-in-valve type container having an MBU actuator having an insert diameter of 0.13". The container has a fill volume of 150 ml and a brimful capacity of 270 ml. As a result a spray pattern of 7 cm is achieved at 10 cm spray distance away from the skin. Such a spray pattern results in an even coating of the composition that can remove hair from the skin in less than 3 minutes.

A rheology assessment of the composition manufactured in Example 1 was carried out with comparison to prior art depilatory compositions. The results are given in FIG. 1. It can be seen from FIG. 1 that the composition according to the present invention has a sharper yield point than prior art depilatory formulations. The sharper yield point indicates that the composition according to the present invention breaks down under stress faster.

The invention claimed is:

1. A sprayable depilatory composition comprising:
   a depilatory agent;
   a surfactant comprising ceteareth 20, cetearyl alcohol, and stearyl ether, wherein the surfactant is present in the range of 0.1% to 3.5% by weight of the composition; and
   a pH regulator to maintain the pH of the composition at a value greater than 5;
   wherein the surfactant comprises ceteareth 20 present in an amount of not more than about 1.0% by weight of the composition;
   wherein the surfactant comprises cetearyl alcohol in an amount of less than about 2.2% by weight of the composition;
   wherein the surfactant comprises stearyl ether in an amount of less than about 0.6% by weight of the composition;
   wherein the composition has a viscosity in the range of about 1.0 Pas to about 5.00 Pas;
   wherein the depilatory agent comprises one or more depilatory actives selected from the group consisting of thioglycolic acid, cysteine, glutathione, N-acetyl-L-cysteine, lipoic acid, thiosalicylic acid, and thiolactic acid, and cosmetically- and/or pharmaceutically-acceptable salts thereof; and
   wherein the composition comprises the one or more depilatory actives in an amount of 8.0% to 14% by weight.

2. A composition according to claim 1 wherein the composition has a viscosity in the range of about 1.0 to about 4.5 Pas.

3. A composition according to claim 1, wherein the composition has a viscosity in the range of about 1.5 Pas to about 4.5 Pas.

4. A composition according to claim 1, wherein the surfactant further comprises cetearyl phosphate, cetearyl glycoside, cetostearyl alcohol or mixtures thereof.

5. A composition according to claim 4, wherein the surfactant comprises cetearyl alcohol present in an amount less than 0.6% by weight of the composition.

6. A composition according to claim 1, wherein the depilatory agent comprises one or more depilatory actives selected from the group consisting of thioglycolic acid, cysteine, glutathione, N-acetyl-L-cysteine, and cosmetically- and/or pharmaceutically-acceptable salts thereof.

7. A method of depilation comprising:
   a. providing a dispensing apparatus having a spray nozzle, the dispensing apparatus containing a depilatory composition according to claim 1;
   b. dispensing the depilatory composition from the dispenser through the nozzle so as to form a substantially uniform layer of composition over an area of hairy skin;
   c. permitting the composition to remain on the skin for a residence time so as to degrade the hairs;
   d. removing the composition together with the depilated hairs at the end of the residence time;
   e. rinsing the skin.

8. A method of degrading hair, the method comprising: applying, to the hair, the composition according to claim 1 so as to degrade hair.

9. A hair removal system comprising:
   a dispensing apparatus having an internal reservoir and an actuator having a diameter in the range 0.01" to 0.017", the dispensing apparatus having an internal pressure, prior to first use, in the range of 4 to 9 bar; and
   a depilatory composition according to claim 1.

10. A sprayable depilatory composition comprising:
    a depilatory agent;
    an accelerator selected from the group consisting of urea, thiourea, dimethyl isosorbide, ethoxydiglycol and methyl propyl diol;
    a surfactant comprising ceteareth 20, cetearyl alcohol, and stearyl ether, wherein the surfactant is present in the range 0.1% to 3.5% by weight of the composition; and
    a pH regulator to maintain the pH of the composition at a value greater than 5;
    wherein the surfactant includes ceteareth 20 present in an amount of not more than about 1.0% by weight of the composition;
    wherein the surfactant comprises cetearyl alcohol in an amount of less than about 2.2% by weight of the composition;
    wherein the surfactant comprises stearyl ether in an amount of less than about 0.6% by weight of the composition;
    wherein the composition has an initial viscosity in the range of about 1.0 to about 5.00 Pas.

11. The sprayable depilatory composition of claim 10, wherein:
    the composition comprises from 7% to 10% by weight of the accelerator; and
    the pH regulator maintains the pH of the composition at a value of between 12 and 12.7.

* * * * *